United States Patent [19]
Vandewalle

[11] Patent Number: 5,810,821
[45] Date of Patent: Sep. 22, 1998

[54] BONE FIXATION SCREW SYSTEM

[75] Inventor: Mark V. Vandewalle, Pierceton, Ind.

[73] Assignee: Biomet Inc., Warsaw, Ind.

[21] Appl. No.: 828,406

[22] Filed: Mar. 28, 1997

[51] Int. Cl.$^6$ .................................................... A61B 17/56
[52] U.S. Cl. ................................ 606/65; 606/73; 606/77; 606/80
[58] Field of Search .................................. 606/65, 66, 67, 606/68, 69, 70, 71, 72, 73, 77, 79, 80

[56] References Cited

U.S. PATENT DOCUMENTS

| | | |
|---|---|---|
| 3,103,926 | 9/1963 | Cochran et al. . |
| 4,338,926 | 7/1982 | Kummer et al. . |
| 4,438,762 | 3/1984 | Kyle ........................................ 606/65 |
| 4,456,005 | 6/1984 | Lichty . |
| 4,776,329 | 10/1988 | Treharne . |
| 4,840,632 | 6/1989 | Kampner . |
| 4,973,333 | 11/1990 | Treharne . |
| 5,169,400 | 12/1992 | Muhling et al. . |
| 5,246,441 | 9/1993 | Ross et al. . |
| 5,360,448 | 11/1994 | Thramann . |
| 5,364,400 | 11/1994 | Rego, Jr. et al. . |
| 5,470,334 | 11/1995 | Ross et al. . |
| 5,505,736 | 4/1996 | Reimels et al. . |
| 5,522,817 | 6/1996 | Sander et al. . |

OTHER PUBLICATIONS

Surgical Technique Biomet Compression HIP Screw System Biomet Inc. Warsaw In 48580 Form No. Y–BMT–415/031595/M 1995.

*Primary Examiner*—Guy V. Tucker
*Attorney, Agent, or Firm*—Ernest E. Helms

[57] ABSTRACT

A bone fixation screw system and method of utilization thereof is provided for a bone having first and second sections with a fracture interface there between. A preferred embodiment of the bone fixation screw system includes a side plate having a first part for placement adjacent the bone second section and a second part angled from the first part providing a barrel. The barrel is adapted for insertion into a transsectionally extending bore into the bone in at least the second section of the bone. A lag screw is also provided for positional retention of the first section of the bone with respect to the second section of the bone. The lag screw also has a first part of a resorbable material for threaded connection of the lag screw within the bore of the bone in at least the first section of the bone, the lag screw having a second part connected with the first part made from a stronger nonresorbable material. The present invention also provides a bone screw having a resorbable material for a threaded first part. The bone screw first part is connected to a nonresorbable bone screw second part.

20 Claims, 4 Drawing Sheets

BONE FIXATION SCREW SYSTEM

BACKGROUND OF THE INVENTION

The present invention relates to a bone fixation screw system The present invention also provides methods of utilization of bone fixation screw systems. More particularly an embodiment of the present invention relates to a compression hip screw system for strong and stable internal fixation for a variety of intertrochanteric, subtrochanteric and basilar neck fractures as well as compression screw systems for superacondylar or "T" condylar fractures about the distal femur.

Bone fixation screw systems are used often for internal fixation of fractures of the hip bone and distal femur. The bone structure typically will have first and second bone sections separated from one another by a fracture interface. The bone second section is the major portion of the bone structure which includes the femoral shaft. A surgeon will drill a transsectional bore into the bone. The bore will go through all of the bone second section and then will typically only partially penetrate into the bone first section. A front portion of the bore in the bone first section is then tapped to provide a female thread therein.

The surgeon then inserts into the bore a lag screw(a specialized form of a bone screw). The lag screw is typically machined from cold worked stainless steel due to strength and biological requirements. The lag screw has an intergral male thread at its forward end. A shank of the lag screw extends rearward from the male threads and passes through the bore in both the first and second bone sections. The lag screw is then rotated by the surgeon to threadably attach the lag screw to the bone first section.

The surgeon then inserts a barrel into a rear end of the bore in the second bone section. Typically the barrel will have an internal diameter with opposed flats that match longitudinal flats on the lag screw. Alignment of the flats on the lag screw and barrel prevent the lag screw from rotating. Therefore the lag screw cannot be inadvertently released from the first bone section.

The barrel is integrally connected with a side plate. The side plate is angled from the barrel. The side plate extends along a side of the second section of the bone parallel to a major axis of the bone second section. The surgeon then attaches the side plate to the second section (femoral shaft) of the bone via a series of mounting screws. The lag screw on its rear end has an internal bore previously tapped with a female thread. A shank of a compression screw is threadably connected with the rear end of the lag screw. A head of the compression screw is seated against a counter bore seat of the barrel. Torquing the compression screw causes the lag screw to be pulled rearward and places the first bone section in compression against the fracture interface. The amount of compression utilized will be determined by the surgeon.

After the fracture has sufficiently healed it is sometimes desirable to remove the lag screw. To remove the lag screw the compression screw is threadably released from the lag screw. The side plate must then be removed from the side of the bone by removal of its mounting screws. As the side plate is removed, the barrel will be rearwardly pulled out of the bore in the second bone section.

In the healing process the bone will grow into the female threads that were tapped in the first and second bone sections, locking the lag screw in position. Therefore the lag screw cannot be simply rotated to threadably release the lag screw from the bone first section. To release the lag screw a trephine is fitted over the lag screw. The trephine is used to cut a core of bone surrounding the lag screw to allow release of the lag screw. A more detailed review of the present state of the art can be gained by a review of the surgical technique of Frank R. Ebert M.D. Baltimore Md., as described in Biomet Brochure YBMT-415/031595/M © 1995 Biomet, Inc. Warsaw Ind. 46580.

Although excellent results have been achieved with the above noted process it would be desirable to modify the lag screw removal process. The above noted lag screw removal process requires the cutting of additional bone tissue, after a prior healing process. Furthermore the side plate and barrel must be removed before the lag screw can be removed.

It would be desirable to provide a bone fixation screw system wherein the lag screw would have sufficient strength and wherein the lag screw could be removed without the use of a trephine. It would also be desirable to have a bone fixation screw system which allows removal of the lag screw without removal of the barrel and side plate.

SUMMARY OF THE INVENTION

To meet the above noted desires, the present invention is brought forth. In a preferred embodiment, the present invention provides a bone fixation screw system which includes a side plate having a first part for placement adjacent the bone and a second part angled from the first part providing a barrel. The barrel is inserted into a bore of the bone. The bore in the bone intersects a first and second section of the bone that are separated by a fracture interface. A lag screw is threadably connected into the bore in the bone first section. The lag screw of the present invention at a front end has a male thread of a resorbable plastic material. The resorbable material is connected to a stronger metal shaft which includes a shank and a reduced diameter stud. The stud projects forward from the shank. The stud is also surrounded by the male threads.

After sufficient healing of the bone has occurred, the male threads will be absorbed into the bone. The side plate can remain attached to the bone and the lag screw can be simply pulled out in a rearward direction for removal.

DETAILED DESCRIPTION OF THE PRFERRED EMBODIMENTS

Figure 1:
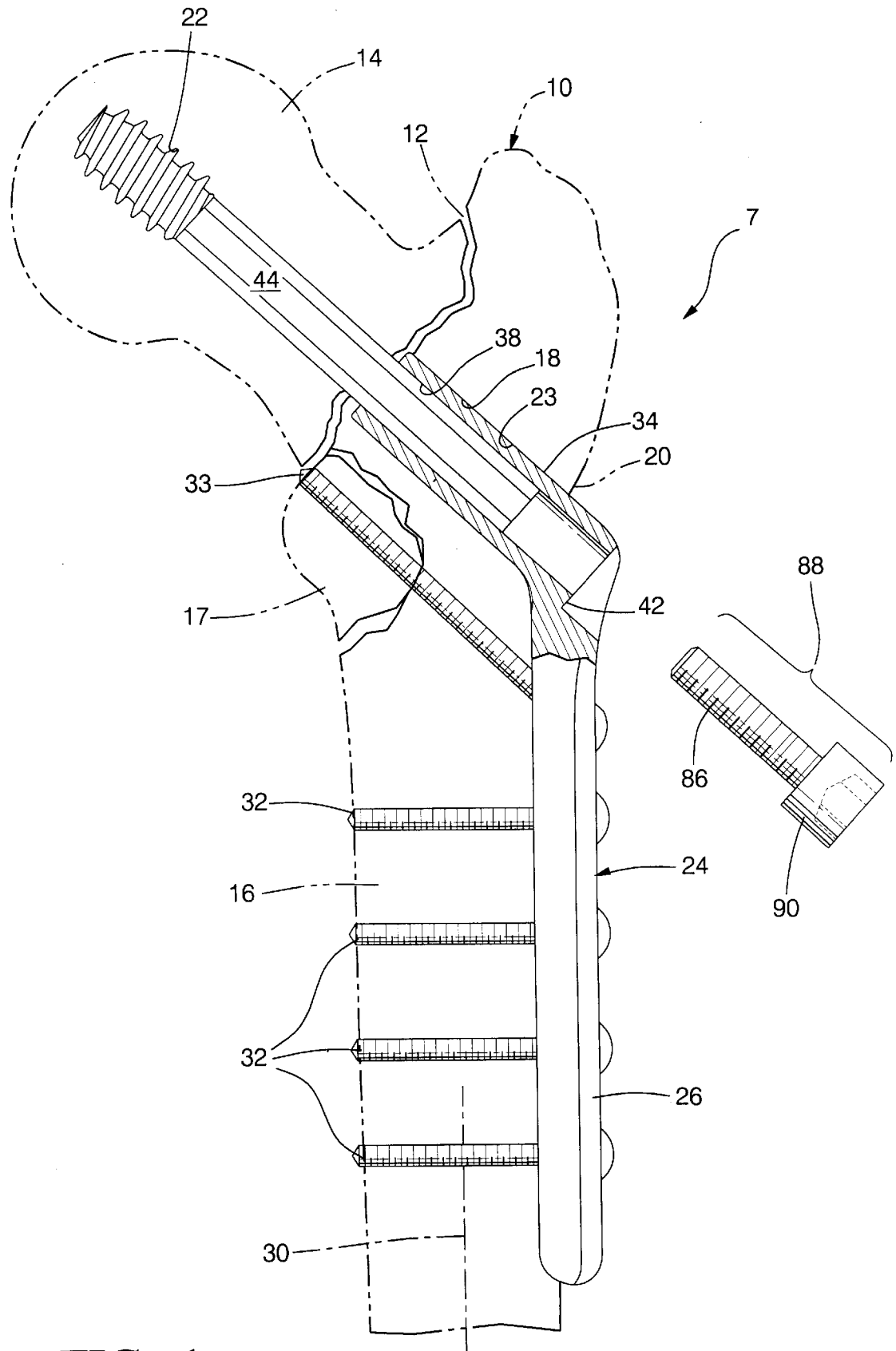
FIG. 1 is a side elevation view of a preferred embodiment of the present invention with portions partially sectioned.
Figure 2:
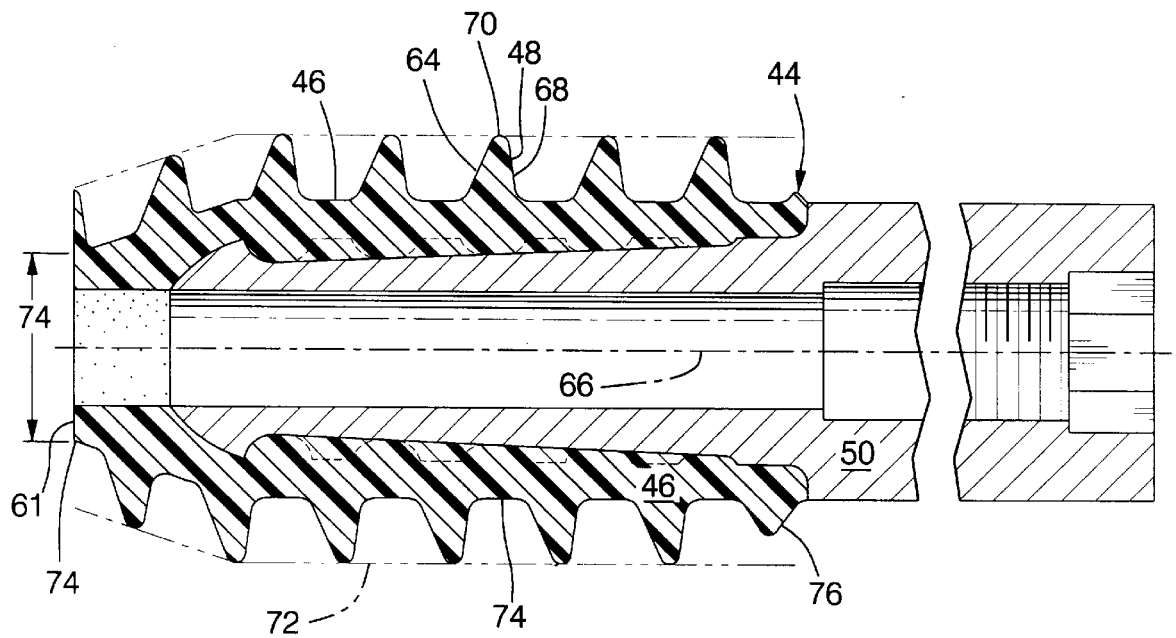
FIG. 2 is a side sectional view of a lag screw with a first part with resorbable male threads connected to a second nonresorbable part of the lag screw.

FIG. 1 illustrates a top of a femur 10 (shown in phantom) having a femoral neck fracture 12 providing an interface between a first bone section or s femoral head 14 and a second bone section or femoral shaft 16. A transsectional bore 18 is drilled from a rear surface 20 of the femoral shaft intersecting the fracture 12 and then penetrating into the femoral head 14. The bore 18 in the femoral head 14 is tapped to have a female thread in a region 22. The bore 18 in a region 23 of the femoral shaft can be reamed to have a slightly larger diameter if desired.

Figure 7:
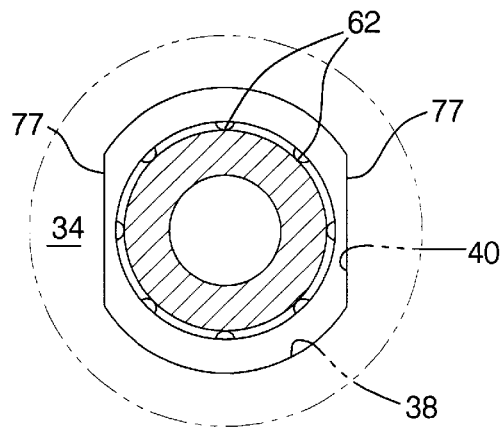
Figure 8:
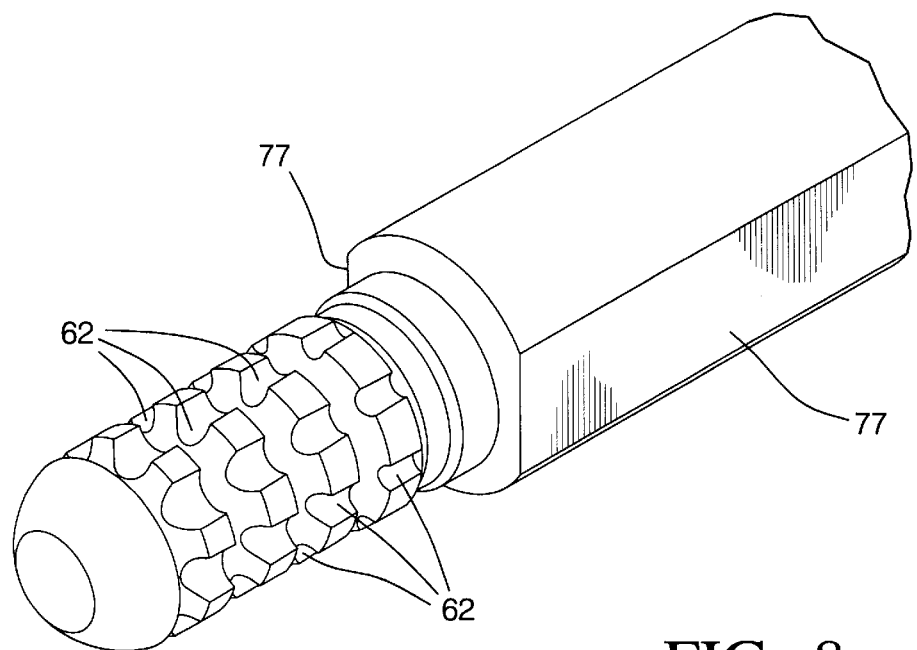
FIG. 8 is a perspective view of the lag screw shown in FIG. 3.

A bone fixation screw system 7 according to the present invention provides a side plate 24. The side plate 24 has a first part 26 for placement adjacent a side of the femoral shaft 16 generally parallel to a major axes 30 of the femur. The side plate 24 is mounted to the femoral shaft 16 by a series of self tapping screws 32. A screw 33 can be used for positional fixing of another minor section 17 of the femur if appropriate. Angled from the side plate first part 26, is a side plate second part or barrel 34. The barrel 34 is integrally connected with the side plate first part 26. The barrel 34 is inserted into the bore 18 from the rear surface 20 of the femur shaft adjacent the femur lateral cortex. The angle the barrel 34 makes with the side plate first part 26 is a matter of selection by the surgeon and typically will be between 150–130 degrees for hip applications. For superacondylar (knee joint applications, not shown) the angle is typically 95 degrees. The barrel 34 (FIG. 7 in phantom) has an interior diameter 38 with two opposing flats 40. The barrel 34 also has adjacent a rear end a counter bore seat 42

Referring additionally to FIGS. 2–8, the second major component of the bone fixation system 7 is a lag screw 44. The lag screw 44 at an extreme forward end has a first part 46 made of the resorbable material. The material can be a plastic such as a copolymer of L-lactic acid and glycolic acid or other suitable alternatives.

Figure 3:
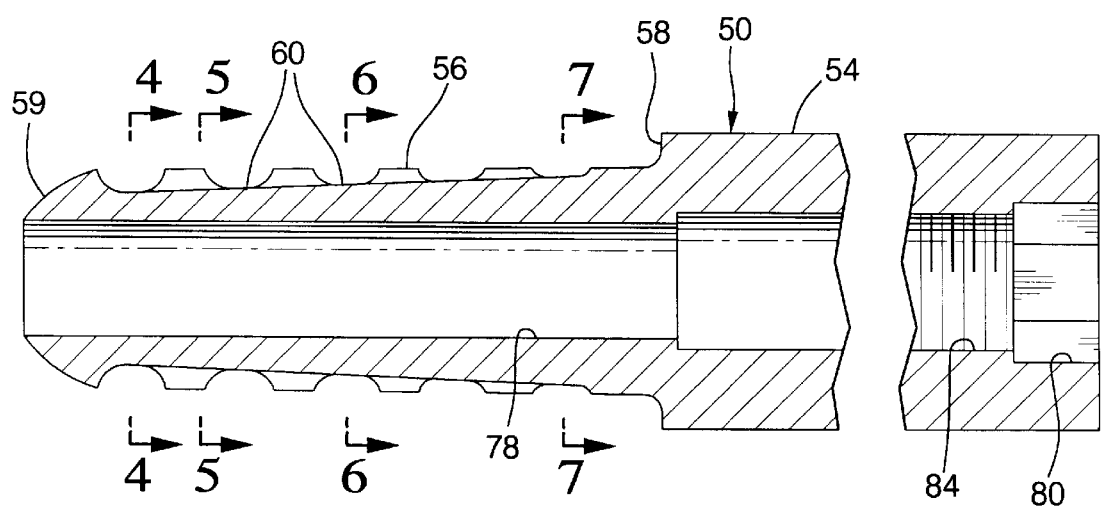
FIG. 3 is a view similar to FIG. 2 with the resorbable threads removed.
Figure 4:
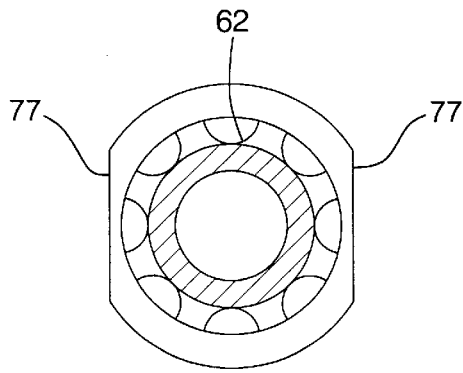
FIGS. 4–7 are views taken along lines 4—4; 5—5; 6—6 and 7—7 respectively.
Figure 5:
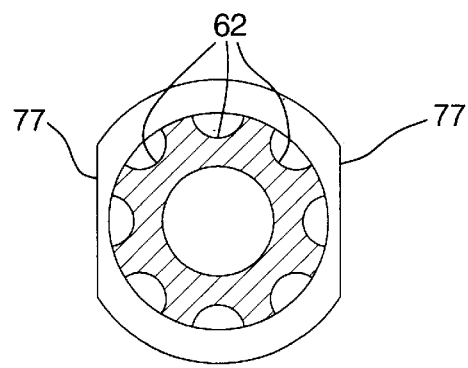
Figure 6:
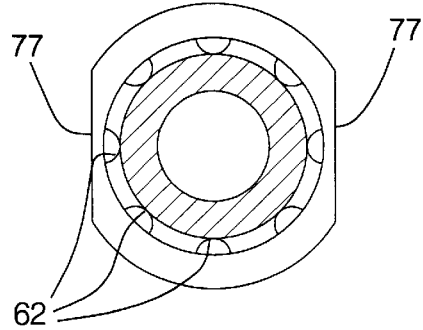

The lag screw first part 46 is connected in a torsionally fixed manner with a nonresorbable material second part 50 (FIG. 3). The lag screw second part 50 is machined from a material that is stronger than the material which is used for the lag screw first part 46. The lag screw second part 50 is typically made from the same material that the side plate 24 is made of which is a 316 stainless steel. An outer diameter of the lag screw second part 50 will typically be 12 to 20 millimeters. The lag screw second part 50 must be strong enough to support the femoral head 14 and typically must withstand stress of 90,000 lbf. per square inch. Therefore allowing the lag screw second part 50 to be fabricated from a metal instead of a lower strength material allows the lag screw second part 50 diameter to remain relatively small.

The lag screw second part 50 has a shank 54 with a reduced diameter section or integral stud 56 that extends from its forward extreme end. The stud 56 has a shoulder 58 where it joins the shank 54. The shoulder 58 helps to prevent the first part 46 from a being pushed off the stud 56 during insertion.

The stud 56 has a slightly reducing taper, as it extends forward, allowing the stud 56 to have its greatest diameter in the area of greatest stress. An extreme front end 59 of the stud is radiused to reduce any stress in the interface between the metal stud 56 and the plastic first part 46.

The stud 56 has a series of radial or annular grooves 60 to provide a plurality of tongue and groove connections with the surrounding first part 46. The tongue and groove connections aid in the axial retention of the lag screw first part 46 to the stud 56. The depth of the grooves 60 progressively increases as the grooves 60 are closer to the stud extreme front end 59, thereby maximizing the diameter of the stud 56 in the regions of greatest stress.

The stud 56 also has a series of geometrically spaced axial longitudinal grooves 62 ( shown best in FIGS. 4–8) which provide a torsional tongue and groove combination with the lag screw first part 46. The grooves 62 aid in the impartation of torque from the lag screw second part 50 to the lag screw first part 46. In a manner similar to the grooves 60, the depth of the grooves 62 progressively increases in the direction toward the stud extreme front end 59.

A male thread 48 has a front face 64 that is inclined with respect to a longitudinal axis 66 of the lag screw. A rear thread face 68 is generally perpendicular to the longitudinal axis 66. A thread crest 70 is radiused as well as both of the bases of the thread faces 64 and 68. The radius of the crest 70 and of the base of the threads faces 64 and 68 are somewhat increased as compared to radiuses of metallic screw threads. The increased radius dimensions facilitate strength and molding considerations of the plastic material of the lag screw first part 46.

An extreme front end 61 (FIG. 2) of the lag screw first part 46 extends forward from the extreme end 59 (FIG. 3)of the stub 56. A thread outer and inner diameter 72 and 74 excursions are truncated at an extreme front end. The reduction of the inner thread 74 diameter facilitates easier insertion of the lag screw 44. The thread outer diameter 72 is truncated at a rear end 76. The thread outer diameter 72 is typically larger than any diameter of the lag screw second part 50 or the inner diameter 38 of the barrel 34.

The shank 54, on a major and preferably entire portion of its exterior length has two longitudinal flats 77 which align with the flats 40 of the barrel. The lag screw 44 has a central longitudinal bore 78 which facilitates installation of the lag screw along a guide pin (not shown). At a rear end, the lag screw 44 has an internal hexagonal socket 80 for receipt of a driver (not shown) during installation or removal. The bore 78 is tapped to insert a female thread 84 for receipt of a shank 86 of a compression screw 88 (FIG. 1).

In operation the bore 18 is drilled and tapped with a female thread in region 22. The female thread will typically have a diameter equal to the diameter of the male thread 48. The lag screw 44 is threadably connected with the femoral head 14 with careful attention being given to proper alignment of the flats 77. The barrel 34 is then inserted into the bore 18, thereby encircling and locking the lag screw 44 from rotation and thereby preventing inadvertent removal of the lag screw 44.

The side plate first part 26 is then mounted to the femoral shaft 16 by the screws 32. The compression screw shank 86 is then torqued into the female thread 84 of the lag screw with a head 90 of the compression screw mating against the counter bore seat 42 of the barrel. The surgeon will torque the compression screw 88 to pull on (tension) the lag screw 44 to set the compression of the femoral head 14 against the fracture 12 interface.

After the femur 10 has since sufficiently healed, the resorbable thread 48 will partially or totally dissolve. Should the surgeon desire to remove the lag screw 44, the compression screw 88 is removed. The lag screw 44 can then be pulled out rearward through the barrel 34. The side plate first part 26 and barrel 34 can remain attached. The above noted procedure is a far less complex operating procedure than would be required for removal of the side plate barrel.

The above treatment procedure assumes familiarity with how to expose the femur, properly measure and determine the type of fracture, properly reduce the fracture, drill a transsectional bore and tap the same, install guide pins, and utilize other various surgical instruments as required for a proper procedure.

Figure 9:
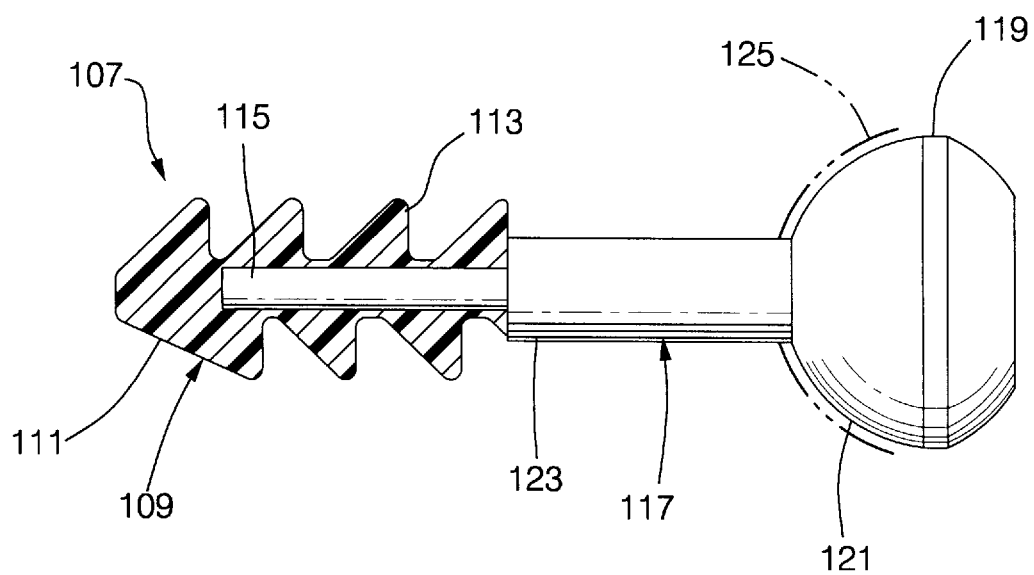
FIG. 9 is a side elevation view, partially sectioned, of a bone screw.

FIG. 9 illustrates a bone screw 107. The bone screw 107 has a resorbable plastic first part 109 having a tip 111 and a screw thread 113. A metallic nonresorbable second part 117 has a forward extending reduced diameter stud 115, a shank 123 and a rear end head 119. A shoulder separates the stud 115 from the shank 123. The first part 109 surrounds the stud 115. The head 119 has a spherical portion 121 that is typically seated in a counter bore 125 seat (shown in phantom) provided in a section of the bone by a surgeon.

The bone screw 107 can be used to positionally affix two bone sections separated by a fracture interface or to attach a plate to a bone. In cases where a plate is attached to a bone, the head 119 will contact a plate counter bore seat shaped similar to counter bore seat 125 to urge the plate toward the bone.

Figure 10:
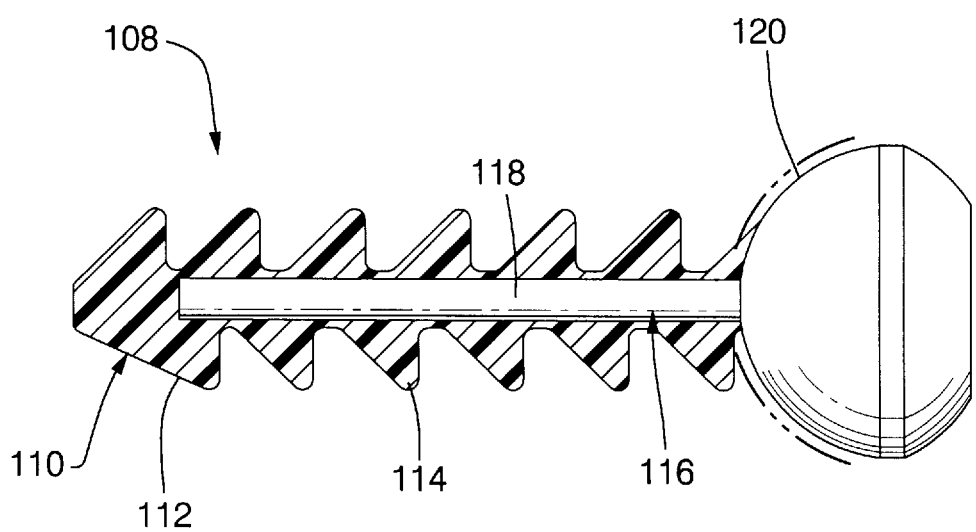
FIG. 10 is a side elevation view, partially sectioned, of an alternate bone screw.

In a similar manner as described above a bone screw 108 (FIG. 10) can be utilized. The bone screw 108 has a resorbable first part 110. The first part 110 has a tip 112 joined to a thread 114. The bone screw has a second nonresorable part 116. The bone screw second part 116 has a shank 118 joined to a head 120. Removal of bone screws 107 or 108 is made easier then that of conventional bone screws due to the fact that the screw threads 113, 114 are resorbable in a manner as previously described for the lag screw first part 46 in FIGS. 1–8.

In accordance with the provisions of the patent statutes, the principle and mode of operation of this invention have been explained and illustrated in its preferred embodiment. However, it must be understood that this invention may be practiced otherwise than as specifically explained and illustrated without departing from its spirit or scope.

What is claimed is:

1. A bone fixation screw system for a bone having first and second sections with an interface there between, the bone fixation screw system comprising comprising:
    a side plate having a first part for placement adjacent the bone second section and a second part angled from the first part providing a barrel, the barrel being adapted for insertion into a transsectionally extending bore into the bone in at least the second section of the bone; and
    a lag screw for positional retention of the first section of the bone with respect to the second section of the bone, the lag screw having a first part of a resorbable material for threaded connection of the lag screw within the bore of the bone in at least the first section of the bone, the lag screw having a second part connected with the first part made from a stronger nonresorbable material.

2. A bone fixation screw system as described in claim 1 wherein the second part of the lag screw is made from a metal.

3. A bone fixation screw system as described in claim 1 wherein the lag screw first part surrounds the lag screw second part at an extreme end of the lag screw second part.

4. A bone fixation screw system as described in claim 3 wherein the lag screw first part surrounds a reduced diameter section of the lag screw second part.

5. A bone fixation screw system as described in claim 4 wherein the lag screw second part has a shoulder between the reduced diameter section and the remainder of the second part of the lag screw.

6. A bone fixation screw system as described in claim 4 wherein the lag screw second part reduced diameter section is tapered towards the lag screw second part extreme end.

7. A bone fixation screw system as described in claim 3 wherein the lag screw second part that is surrounded by the lag screw first part, has a torsional tongue and groove connection with the lag screw first part to aid impartation of torque between the second and first parts of the lag screw.

8. A bone fixation screw system as described in claim 7 wherein the lag screw has an axial longitudinal groove in the lag screw second part and a depth of the axial longitudinal groove in the lag screw second part is progressively increased toward the extreme end of the lag screw second part.

9. A bone fixation screw system as described in claim 3 wherein the lag screw second part that is surrounded by the lag screw first part, has a generally annular tongue and groove connection with the first part to aid axial retention of the lag screw first part to the lag screw second part.

10. A bone fixation screw system as described in claim 9 wherein there are a plurality of annular grooves on the lag screw second part and respective depths of the annular grooves are progressively increased towards the extreme end of the lag screw second part.

11. A bone fixation screw system as described in claim 3 wherein a section of the lag screw second part that is not surrounded by the first part has at least one exterior longitudinal flat along an entire length.

12. A bone fixation screw system as described in claim 1 wherein the lag screw second part can translate through the side plate barrel.

13. A bone fixation screw system as described in claim 12 wherein the lag screw second part is locked from rotation by the side plate barrel.

14. A bone fixation screw system as described in claim 1 further including a compression screw that sets the position of the lag screw with respect to the barrel of the side plate.

15. A bone fixation screw system for a bone having first and second sections with an interface there between, the screw system comprising:
    a side plate having a first part for placement adjacent the bone second section and a second part angled from the first part providing a barrel, the barrel being adapted for insertion into a transsectionally extending bore of the bone in at least the second section of the bone; and
    a lag screw for positional retention of a bone having first and second sections with an interface there between, the lag screw including a first part of a resorbable material for threaded connection of the lag screw within the transsectionally extending bore of the bone in at least the first section of the bone, and the lag screw also having a second part made from a stronger nonresorbable metallic material, the lag screw second part having an elongated shank with a reduced diameter stud at an extreme end surrounded and connected with the first part, the stud having a torsional tongue and groove connection with the lag screw first part for impartation of torque to the lag screw first part, and the stud having a generally annular tongue and groove connection with the lag screw first part to aid axial retention of the lag screw first part and wherein the lag screw shank has an exterior longitudinal flat and the shank can be translated through the side plate barrel.

16. A method of treating a bone with first and second sections separated by an interface there between with a fixation screw system comprising:
    drilling a transsectionally extending bore through the bone penetrating into the first and second sections;
    threadingly connecting within the transsectionally extending bore of the first bone section, a lag screw with a first part having a male thread of resorbable material and a lag screw second part connected with the first part of a second stronger nonresorbable material;
    encircling the lag screw with a barrel of a side plate, the barrel being inserted into the bore of the bone in at least the second section of the bone; and locationally attaching the side plate with the second section of the bone.

17. A method of treating a bone with first and second sections separated by an interface there between with a fixation screw system as described in claim 16 further including rotatively locking the lag screw with the barrel of the side plate.

18. A method of treating a bone with first and second sections separated by an interface there between with a fixation screw system as described in claim 16 further including removing the lag screw through the barrel of the side plate without removing the side plate from second section of the bone.

19. A method of treating a bone with first and second sections separated by an interface there between with a fixation screw system as described in claim 18 further including tapping a female thread diameter in the first bone section that is greater than a diameter of the lag screw second part or an inner diameter of the barrel, and threadably connecting a lag screw with a first part with a thread having a diameter greater than the inner diameter of the barrel and at least allowing the resorbable first part of the lag screw first part to partially dissolve before removing the lag screw.

20. A method of treating a bone with first and second sections separated by an interface there between with a fixation screw system as described in claim 16 further including setting the relative position of the bone first section with respect to the second position by a compression screw contacting the side plate and lag screw.

* * * * *